United States Patent [19]
Annis

[11] Patent Number: 5,666,393
[45] Date of Patent: Sep. 9, 1997

[54] METHOD AND APPARATUS FOR REDUCING AFTERGLOW NOISE IN AN X-RAY INSPECTION SYSTEM

[76] Inventor: Martin Annis, 65 Banks St., Cambridge, Mass. 02138

[21] Appl. No.: 658,012

[22] Filed: Jun. 4, 1996

Related U.S. Application Data

[63] Continuation of Ser. No. 197,632, Feb. 17, 1994, abandoned.

[51] Int. Cl.[6] ................................... G01N 23/04
[52] U.S. Cl. ................ 378/57; 378/98.2; 378/98.8
[58] Field of Search ............... 378/57, 98.2, 98.8, 378/146

[56] References Cited

U.S. PATENT DOCUMENTS

| | | | |
|---|---|---|---|
| 4,430,568 | 2/1984 | Yoshida et al. | 378/57 |
| 4,745,631 | 5/1988 | Paolini | 378/146 |
| 4,879,734 | 11/1989 | Schreckendgust | 378/57 |
| 5,091,924 | 2/1992 | Bermbach et al. | 378/57 |

*Primary Examiner*—Craig E. Church
*Attorney, Agent, or Firm*—Cesari & McKenna, LLP

[57] ABSTRACT

An improved X-ray inspection system comprises a pulsed X-ray source configured to emit short, X-ray pulses for reducing afterglow noise. A rotating cylindrical collimator limits the X rays to a pencil-beam, which is directed across and through an object prior to interception by a detector. The detector comprises a plurality of scintillating screens optically coupled to photoemissive detecting elements. When the short X-ray pulses generated by the source are intercepted by the detector, the outputs of the detecting elements are sampled for only a short period of time, which sampling period is immediately followed by a substantially longer quiescent period of time during which the elements are not sampled. Therefore, only a slight portion of the typical afterglow noise occurs during measurement of a useful X-ray signal.

12 Claims, 8 Drawing Sheets

METHOD AND APPARATUS FOR REDUCING AFTERGLOW NOISE IN AN X-RAY INSPECTION SYSTEM

This application is a continuation of Ser. No. 08/197,632 filed Feb. 17, 1994 and now abandoned.

FIELD OF THE INVENTION

This invention relates generally to X-ray systems and, more specifically, to a technique for reducing afterglow noise in X-ray inspection systems.

BACKGROUND OF THE INVENTION

Conventional X-ray inspection systems that are typically used to inspect the contents of objects, such as packages and containers used in the shipment of cargo among sea, land and air ports, include either a "fan-beam" X-ray system employing a "line-of-detectors" X-radiation detector or a "flying-spot" X-ray system, the latter of which is shown in FIG. 1. The flying-spot system 10 typically comprises an X-ray source 12 located at the center of a rotating wheel collimator 14 having a plurality of apertures 15 disposed therein. As the collimator rotates about the source, a cone of X rays is collimated into a pencil-beam by the rotating apertures. A fixed cross-slit collimator 16 may be situated between the rotating wheel collimator and an object 17 to further define the pencil-beam in one dimension. A line of X rays is then formed that sweeps across and through the object, while an X-radiation detector 18 intercepts those X rays exiting the object. The remaining portions of the image are acquired as the object moves past the detector.

The X-ray source 12 used in this conventional pencil-beam system is typically configured to continuously emit X rays in a "steady-state" manner. Typical pulsed X-ray sources cannot be used in this system because they emit X rays in short bursts, followed by periods of quiescence, which are too long to allow rapid image formation. Specifically, the conventional pencil-beam system 10 requires numerous, i.e., 500 to 1000, samples during each sweep of the X-ray beam to acquire sufficient picture elements (pixels) for resolving an image in a brief span of time so as to be useful. The latency between X-ray bursts generated by a pulsed source compels a slow rotation of the rotating wheel collimator 14, thereby resulting in an unacceptably long inspection time for objects. Accordingly, conventional pencil-beam systems are forced to use steady-state X-ray sources.

However, the X rays generated by the steady-state source must be sampled by the detector continuously during the entire time that the pixels are traversed in order to acquire useful data signals. The detector 18 typically includes photomultiplier tubes encompassing scintillating material. When the X rays strike the scintillating material, visible light photons are produced in the material and detected by the photomultiplier tubes which, in turn, generate the data signals needed to form the images. In addition to these light photons, a plurality of delayed light photons are generated that subsist for a time comparable to the time required to sweep the beam across portions of the objects. This source of noise, called "afterglow", adversely affects the signal-to-noise ratio of the conventional X-ray inspection system 10 and is, thus, a limiting factor in the efficiency of that system.

Accordingly, the present invention is directed to providing an improved method and apparatus for reducing afterglow noise in X-ray inspection systems.

SUMMARY OF THE INVENTION

Briefly, the invention resides in an improved X-ray inspection system comprising, inter alia, an X-ray source capable of emitting short, X-ray pulses for reducing afterglow noise associated with prior X-ray inspection systems. A rotating cylindrical collimator preferably limits the X rays to a pencil-beam, which is directed across and through an object for interception by a detector.

In one embodiment of the invention, the X-ray source is a linear accelerator that generates a cone of X-rays from high-energy electron pulses having a repetition rate of between 2,000 and 10,000 pulses per second; however, in an alternate embodiment, a low-energy, X-ray tube may also be used to emit short X-ray pulses. In both cases, the pulsed beams preferably have a duration of a few microseconds and are separated from each other by approximately 100 to 500 microseconds.

The detector preferably comprises a single transmission detector and/or at least one X-ray scatter detector, each of which comprises a scintillating screen optically coupled to photoemissive detecting elements, such as photomultiplier tubes. In accordance with the invention, when the short X-ray pulses generated by the source are intercepted by the detector, the outputs of the photomultiplier tubes are sampled for only a short period of time, which sampling period is immediately followed by a substantially longer quiescent period of time during which the photomultiplier tubes are not sampled. In the illustrative embodiment, the ratio of sampling time to quiescent time is approximately 1:50, which is equivalent to the ratio of the duration of the pulsed beams to their separation. Therefore, only 1/50th of the typical afterglow noise occurs during measurement of a useful X-ray signal.

BRIEF DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
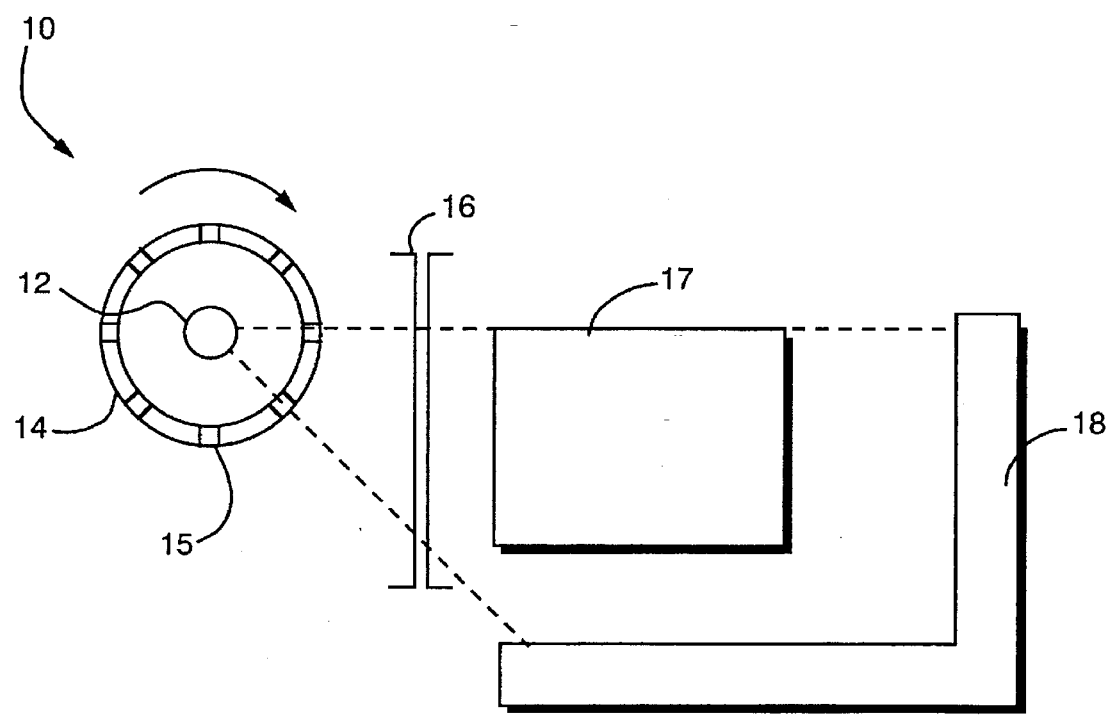
FIG. 1 is a side view of a prior art, pencil-beam X-ray system.
Figure 2A:
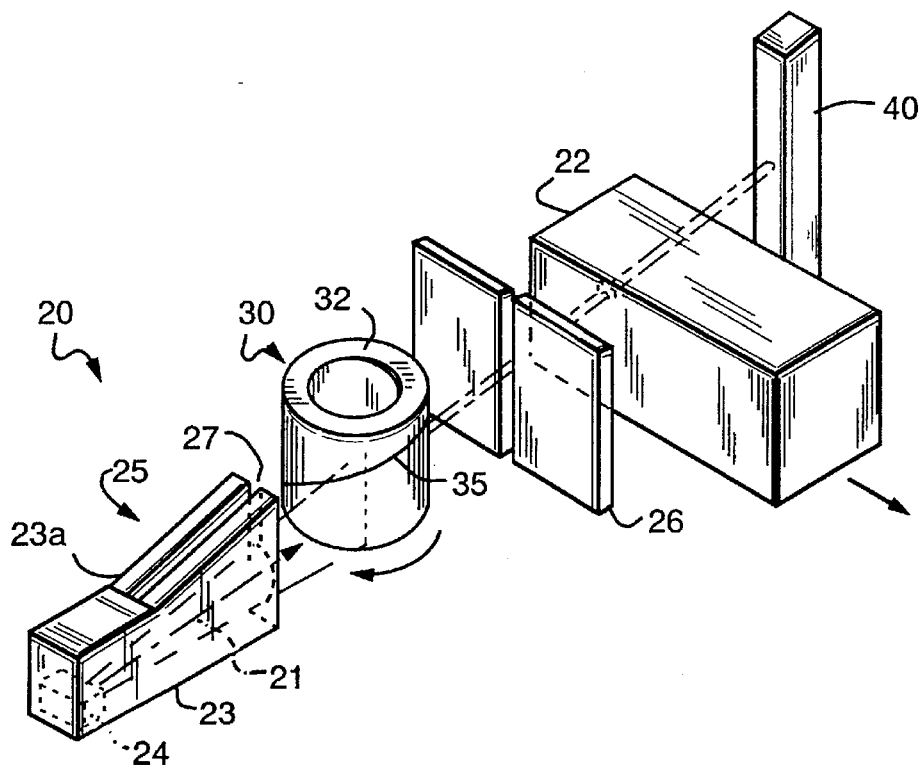
FIG. 2A is an isometric view of an improved X-ray inspection system in accordance with the invention.
Figure 2B:
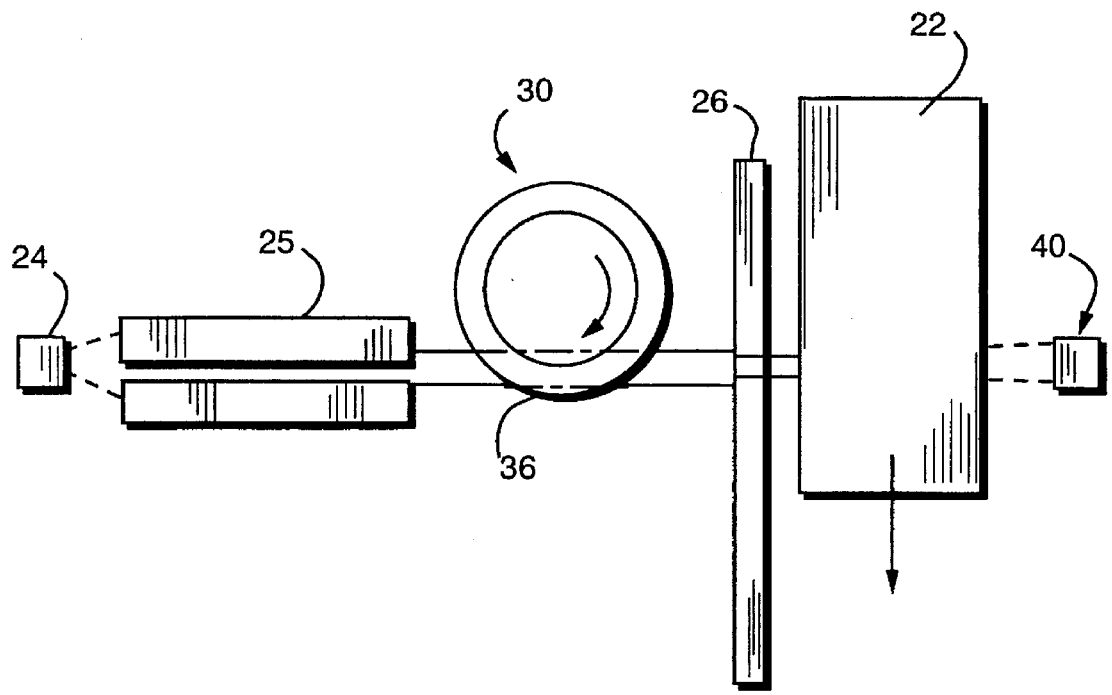
FIG. 2B is a plan view of the improved X-ray inspection system of FIG. 2A.

FIGS. 2A and 2B depict the X-ray inspection system 20 configured for use in accordance with the invention. The elements of the system are not drawn to scale for purposes of ease of depiction and ease of description, although the figures depict their relationship relative to one another. The system 20 is typically used for inspecting the contents of objects 22, such as packages and containers used in cargo shipments, although the system may be employed for other industrial applications, such as for inspecting rockets and large hole castings.

Figure 6:
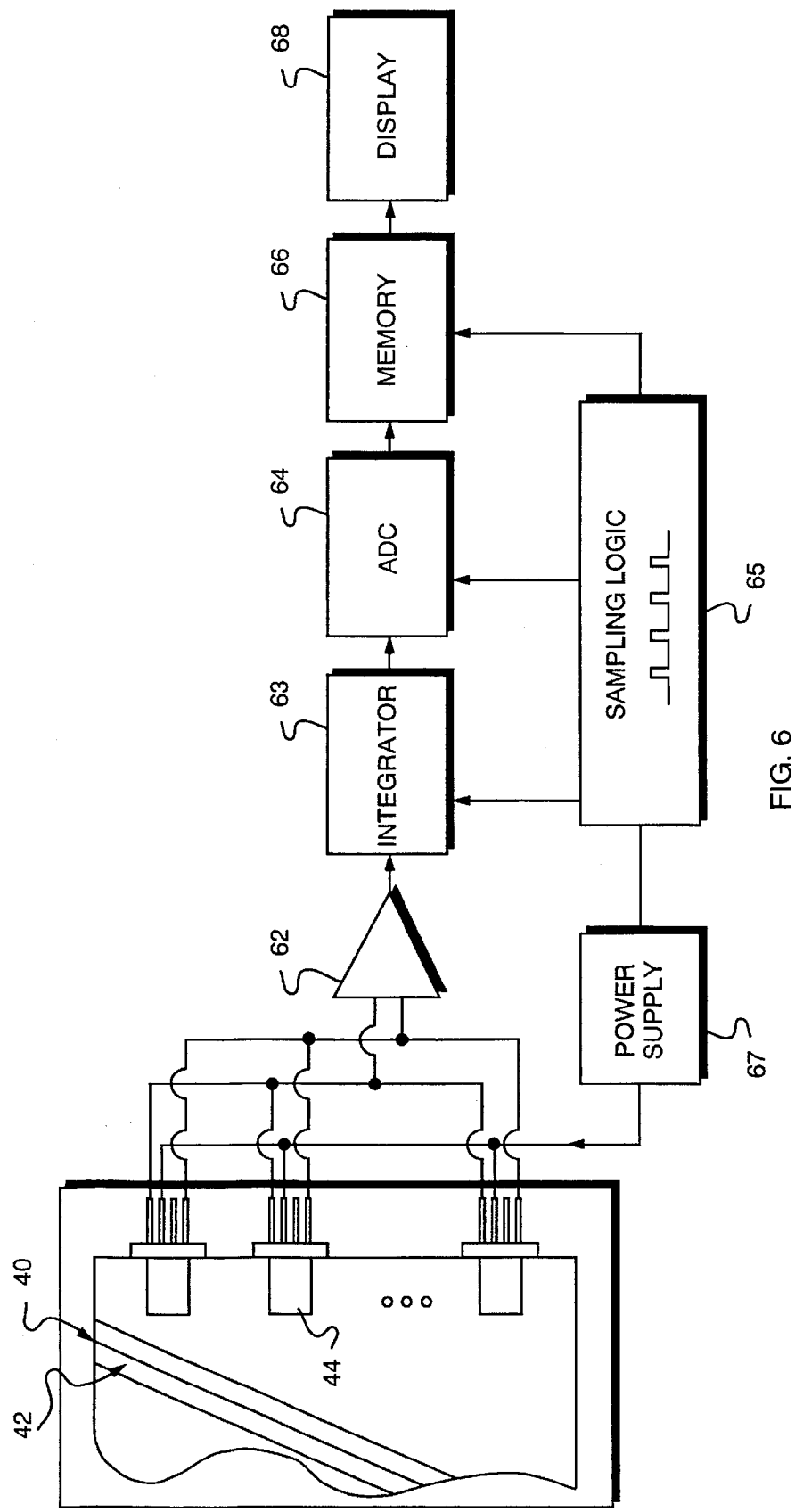
FIG. 6 is a block schematic diagram of an electronic circuit used to control the detector of FIG. 4A.

The inspection system 20 comprises an X-ray source 24 for generating X rays that radiate as a cone. The source is preferably contained within an enclosure 23 having an integrally-formed precollimator 25 that limits the radiated cone along its center axis 21 to form a "fan-beam" of X rays. A rotating cylindrical collimator 30 converts the fan-beam into a pencil-beam of X rays, which may be further limited by a fixed-slit collimator 26. The X-ray beam penetrates the entire area of an object 22 and is intercepted by a detector 40, which transforms the X rays into image data for presentation on a display screen 68 (FIG. 6).

It should be noted that, although the description herein relates to a pencil-beam X-ray system, the invention applies equally to a "fan-beam" X-ray system employing a "line-of-detectors" X-radiation detector.

In the illustrative embodiment of the invention, the X-ray source 24 is a linear accelerator having an X-ray pulse repetition rate of about 2,000 pulses per second (pps). This source is typically used to inspect large objects, such as cargo containers. The accelerator emits a cone of X rays with a peak energy of 9 million electron volts (MeV) and an X-ray flux of approximately 3,000 Roentgens per minute at a distance of one meter on the center axis 21 of the cone. The source radiates a 20° to 40° cone, i.e., 10° to 20° on either side of the center axis 21, which determines the height of the rotating collimator 30 and its distance between the source and object.

Specifically, the accelerator generates pulses of high-energy electrons that impinge upon a target, e.g., a sheet of tungsten 2 mm thick, to produce pulses of X-ray beams. The pulsed beams are preferably asserted for a duration of 2 microseconds (μsecs) and are separated from adjacent pulses by approximately 100 to 500 μsecs. As noted, these high-energy, pulsed X rays may penetrate a cargo container, which typically has a rigid steel frame with rigid corner posts and steel or aluminum infill panels. The containers typically measure 20 or 40 feet in length by 8 feet in height by 8 feet in width. The maximum loaded container weighs approximately 20 tons (20-foot containers) or 40 tons (40-foot containers). A linear accelerator suitable for use as the high-energy X-ray source is a "Mini-Linatron" 6-9-11 MeV linear accelerator manufactured by Varian Inc. of 3045 Hanover Street, Palo Alto, Calif. 94304-1129. When utilized in the system of the invention, these X rays may penetrate up to 15 inches of steel, which represents an increase in penetration over prior inspection systems.

In an alternate embodiment of the invention, the X-ray source 24 is an X-ray tube configured to emit a cone of short X-ray pulses having a peak energy of 600 KeV. As with the high-energy source described above, the pulsed beams generated by this low-energy tube preferably have a duration of a few μsecs and are separated from each other by approximately 100 μsecs. These X rays are typically employed to inspect palletized cargo.

As described further herein, use of a pulsed X-ray source, rather than a steady-state source, significantly improves the penetration capability of the X-ray inspection systems. Because of the "pulsed" nature of such a source, each emitted X-ray pulse may be measured by a reference X-ray detector (not shown) positioned near the X-ray beam leaving the source. A corresponding signal from the detector is processed with the reference detector signal to generate an output pulse having a ratio of the two signals. This effectively compensates for any variations in the output of the source.

The precollimator 25 comprises a large shield 23a with a stationary slit 27 that filters all the radiation emitted by the source except for a preliminary fan-beam of X rays. The stationary shield 23a is typically composed of lead. To efficiently shield a source of radiation, the shield 23a should be close to the source; accordingly, the precollimator 25 is integrally-formed within the enclosure 23 containing the source. In the illustrative embodiment, the enclosure is approximately 4 feet wide, 3 feet high and 8 feet long and, including the accelerator, may weigh between 5 and 10 tons.

The slit 27 is centered along the center axis 21 of the X-ray cone and directs the resulting fan-beam towards the rotating cylindrical collimator 30 and then onto the object 22. To enhance the spatial resolution of an image of the object, the fan-beam should be as thin as possible; however, the beam should be dimensioned to retain sufficient flux to form the image. Therefore, the width of the beam is preferably less than 1 centimeter (cm) as it emerges from the slit 27.

Figure 3A:
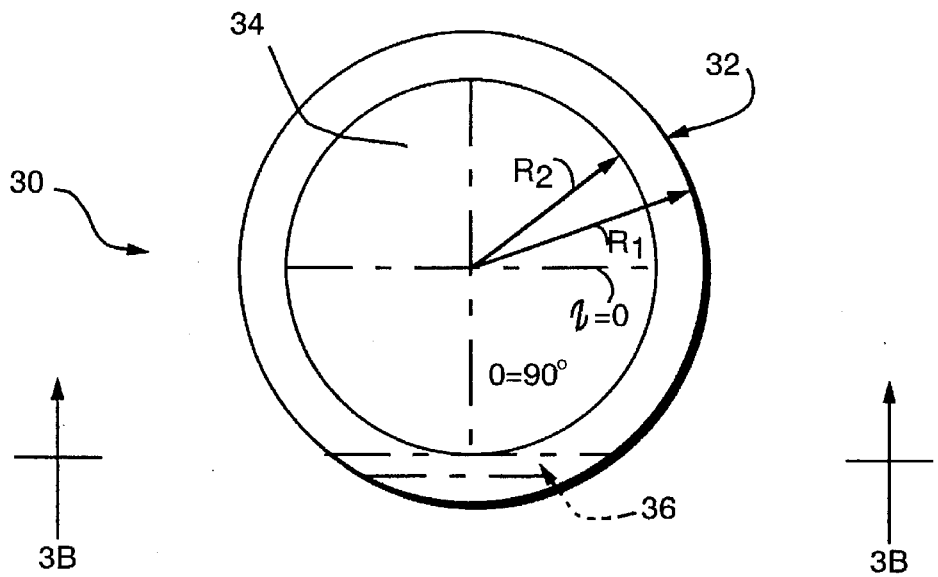
FIG. 3A is a plan view of a rotating cylindrical collimator used in the improved X-ray inspection system of FIG. 2A.

The rotating cylindrical collimator 30 converts the fan-beam into a plurality of pencil-beams that form a sweeping line; however, it should be noted that other similar means may be used to form the pencil-beams. Referring also to FIG. 3A, the collimator 30 is a hollow cylinder with an outer shell 32 and an inner cavity 34, and is constructed of steel. A conventional motor and bearing "on-axis" arrangement (not shown) rotates the collimator at a rate of 2–10 revolutions per second or 120–600 revolutions per minute.

A helical slit 35 extends along the outer surface of the collimator 20. Specifically, the slit 35 is defined by a straight line from the source that penetrates the outer shell 32 and proceeds down its outer surface as the collimator rotates, thus forming a helix around the circumference of the collimator 30. In the illustrative embodiment, the collimator stands 6 feet high and, although the length of the helical slit 35 is slightly less, it is sufficiently long to receive the 40° cone emitted from the source. Preferably, the helical slit 35 is offset a small, predetermined length, e.g., 4 inches, from both the top and bottom of the collimator. Because the collimator is made of steel, these lengths hold the collimator together and simplifies its manufacture.

As the collimator rotates about its center axis, the orientation of the slit changes and the pencil-beams exiting the collimator are constantly displaced in a downward, sweeping direction to form a line of beams. In the illustrative embodiment, each beam exiting the collimator has a cross-sectional area of 0.5 cm by 0.5 cm. Specifically, during each full rotation of the collimator 30, the exiting pencil-beam sweeps from the top of the object 22 to its bottom in 0.1 to 0.5 seconds. The angle of rotation of the rotating collimator determines the height of the pencil-beam impinging the object. The position of each image element (pixel) during a single sweep of the pencil-beam is established by measuring this angle. By moving the object transversely through the beam, lines of data may be recorded to form a two-dimensional, X-ray transmission image of the object.

Figure 3B:
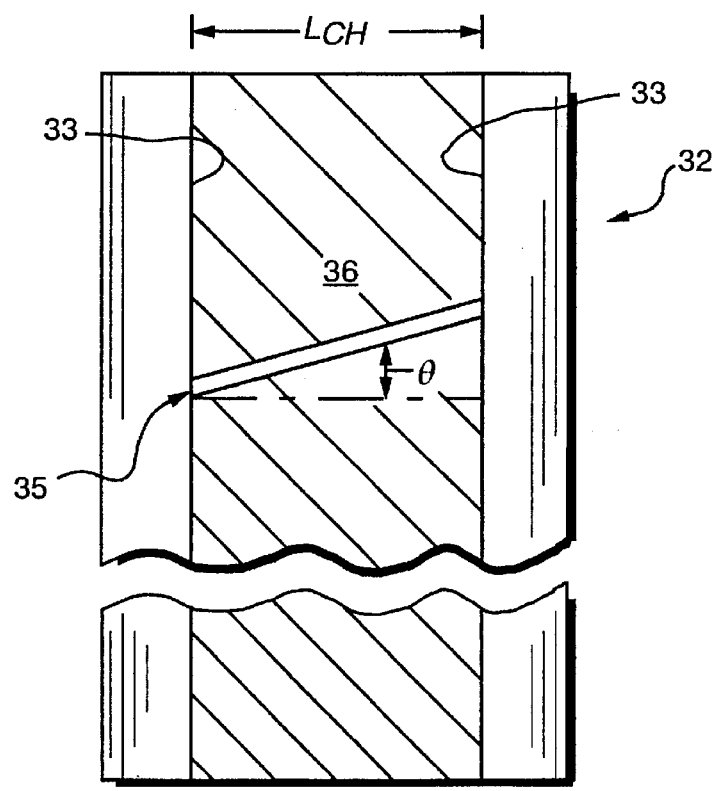
FIG. 3B is a sectional view along line 3A,3A of a chord of the rotating cylindrical collimator of FIG. 3A.

The fan-beam enters the rotating collimator 30 through the helical slit 35 on a chord 36 of the outer shell 32 and exits the collimator through that chord. This is more clearly seen in FIG. 3B, which depicts a cross-section of the chord 36 along the lines 3A,3A (FIG. 3A) of the collimator. Here, the helical slit 35 is shown as having a uniform width that is oriented at an angle Θ which changes as the collimator turns. The fan-beam of X rays exiting the precollimator 25 consists of a plurality of pencil-beams oriented at various angles in a plane generally transvets to the slit 35. Of these angular pencil-beams, only the one that is oriented at the angle Θ is allowed to pass through the slit 35.

The position of the slit 35, i.e., tangent to an inner surface 33 of the collimator, provides a long path length for attenuating X rays which are not part of the desired pencil beam. That is, the length of the cord, $L_{CH}$, is preferably 2.41 feet, which is sufficient to effectively absorb the X rays that are not passed through the slit 35.

Since the angle of rotation of the collimator, i.e., angle φ, is independent of the angle of the pencil-beam in the plane of the collimator, i.e., angle Θ, the velocity of the pencil-beam may be adjusted by altering the angle Θ by changing the location of the slit at discrete points along the shell 32. This enables, e.g., the beam to linger at the bottom and top of the sweeping line of pencil-beams in order to compensate for the decrease in radiation intensity at the edge of the fan-beam. This decrease is characteristic of all linear accelerators and conventional X-ray sources. In addition, the width of the slit 35 may be varied at discrete points along the helix to also alter the radiation intensity at corresponding points along the sweeping line of beams.

Refer again to FIG. 2A. Situated between the rotating collimator 30 and the object 22 is an optional fixed-slit collimator 26 configured to further limit the pencil-beam along the direction of the beam. The fixed-slit collimator 26 is preferably arranged close to the inspected object 22 to ensure that the beam is small along the transverse axis as it impinges the object, thereby improving the resolution of the image. Accordingly, the size of the beam as it impinges the object is preferably less than 1 cm by 1 cm.

As noted, cargo containers are generally standard in size, e.g., 8 feet by 8 feet by various lengths. In the illustrative embodiment, the rotating cylindrical collimator 30 generates an 8 foot vertical sweep of pencil-beams across the front portion of the container 22 every 0.1 seconds. The container is then moved 0.5 cm and another 8-foot sweep is generated. A conventional conveyer system (not shown) moves the object transversely through the pencil-beam of X rays. Preferably, the cargo container moves 40 feet in 200 seconds and the entire container can be scanned in 3.33 minutes.

Figure 4A:
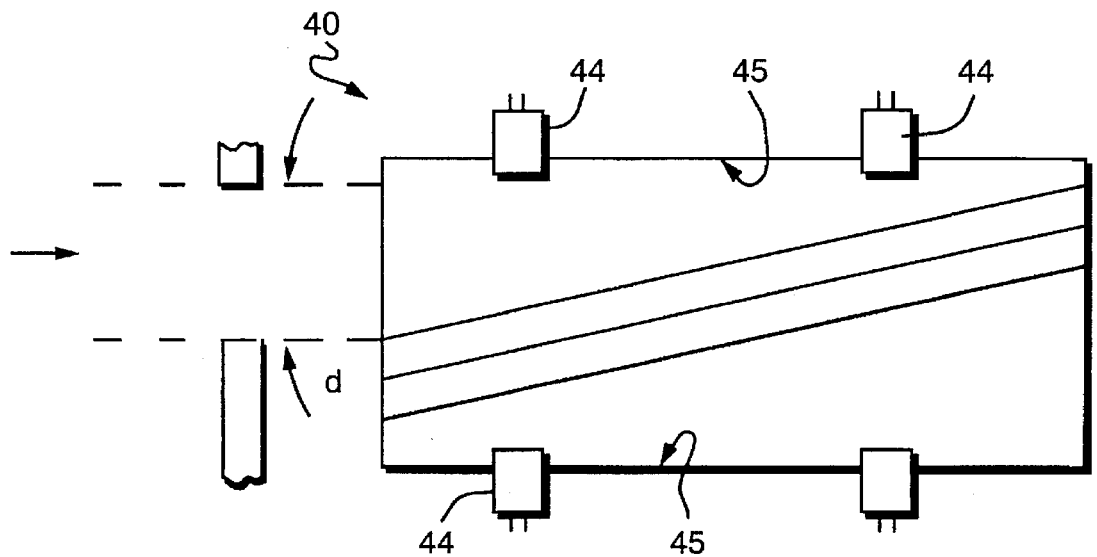
FIG. 4A is a plan view of a detector, including scintillating screens and photomultiplier tubes, for use in the improved X-ray inspection system of FIG. 2A.
Figure 4B:
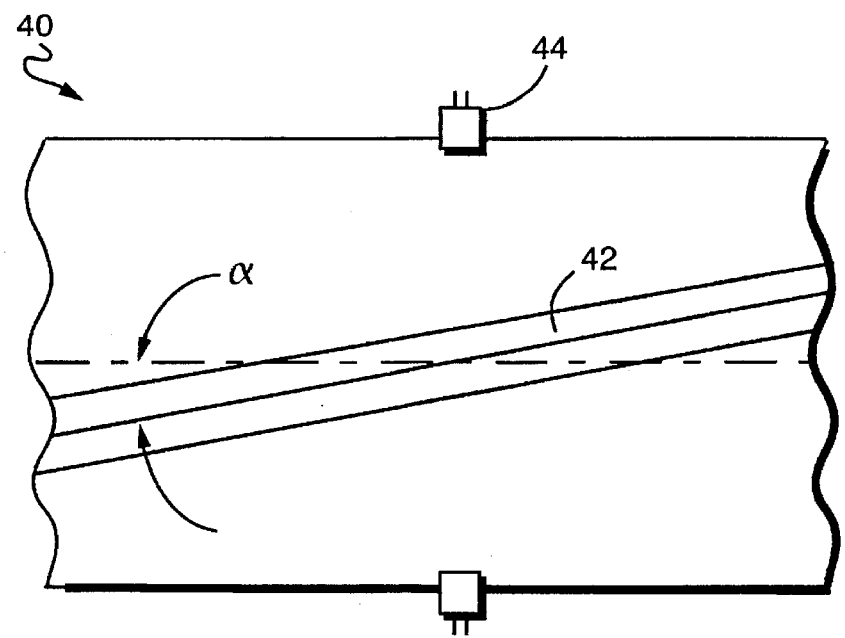
FIG. 4B is a fragmented plan view of the detector showing an X-ray beam penetrating the scintillating screens of FIG. 4A.

After exiting the object 22, the collimated pencil-beam is intercepted by a detector 40, illustrated in FIGS. 4A and 4B. Referring to FIG. 4A, the detector 40 preferably comprises at least one scintillating screen 42 optically coupled to a plurality of photomultiplier tubes 44 disposed along an inner reflecting surface 45 of the detector; however, other photoemissive detecting elements, such as photodiodes, may be used within the teachings of the invention. In the illustrative embodiment, the photomultiplier is 5 inches long with a 3 inch diameter screen. The detector 40 is preferably 2–4 feet deep, 20 feet long and 2 feet wide. The distance d projected by the scintillating screen is 2 cm wide so as to sufficiently encompass the width of the pencil-beam.

The scintillating screen 42 is similar to a conventional screen used in medical applications with film, and is commonly referred to as an "intensifying screen". The X-ray path in the scintillating screen is generally long and may be created by slanting the screen at a small angle with respect to the beam. FIG. 4A shows the beam entering from the left and penetrating two screens 42, each of which have a thickness of 0.5 mm. These screens are relatively opaque to visible light, so the beam must impinge them at a very small angle a, e.g., a 3° angle. Specifically, the scintillating screens 42 are arranged in a back-to-back configuration to increase the efficiency of the detector 40. When the pencil-beam X rays strike the scintillating screen, visible light is produced and detected by the photomultiplier tubes 44 which, in turn, generate signals used to form the X-ray image.

Figure 5:
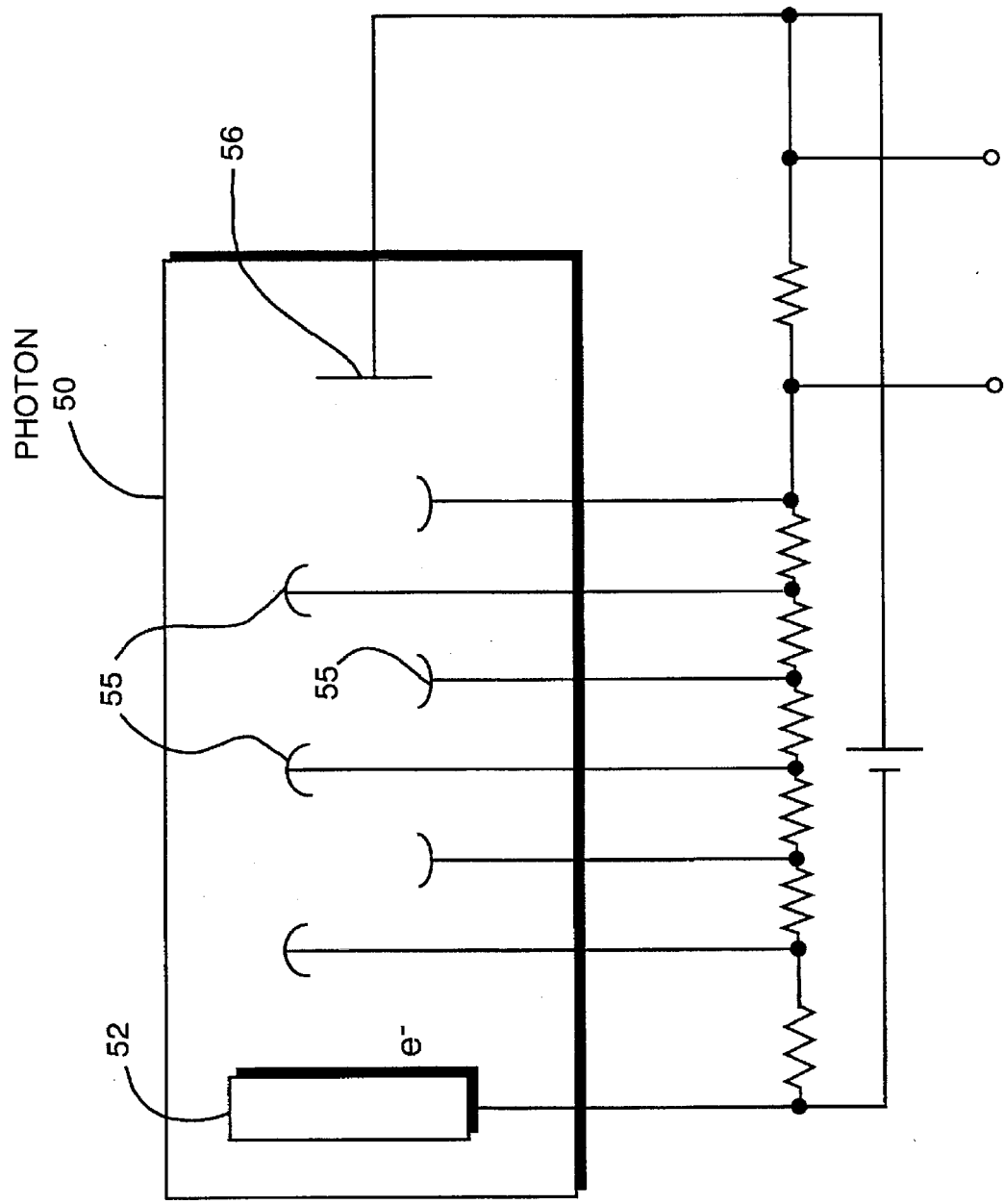
FIG. 5 is a schematized diagram of a photomultiplier tube used in the detector of FIG. 4A.

Broadly stated, the photomultiplier tube 44 is a photocell comprising a vacuum tube and a photosensitive screen for measuring light. As schematically shown in FIG. 5, the vacuum tube 50 contains a photoemissive element 52, e.g., a photocathode, and a string of dynode stages 55 used to amplify current by electron multiplication. The photocathode is preferably semitransparent to enable emission of electrons e– upon incidence of radiation.

Specifically, current is produced when visible light enters the tube and is absorbed by the photoemissive element 52. Each dynode 55 is maintained at a fixed potential relative to the photocathode, with increasing potential along the dynode string to the final collecting electrode or anode 56. This dynode string effectively multiplies electrons such that the gain of the photomultiplier is, e.g., $10^6$. Preferably, there are 32 photomultipliers in the detector.

FIG. 6 is a block schematic diagram of an electronic circuit 60 used to control the detector 40. The photomultiplier tubes 44 are preferably arranged in parallel and supply a net analog signal to an amplifier circuit 62, whose output is provided to an analog-to-digital converter (ADC) 64 via an integrator circuit 63. Sampling logic 65 controls sampling of the outputs of the photomultiplier tubes 44 by the integrator 63 and ADC 64 at a predetermined rate. The resulting digitized signal is provided to a memory 66 for subsequent display on a device, such as a computer screen, as pixels of an image.

It should be noted that the X-ray source 14 preferably emits one pulse per pixel displayed on the display 68; however, this ratio may be altered. The actual number of X-ray photons per pixel that enter the object may be as many as $10^5$; that is, there may be $10^5$ X-ray photons $10^5$ X-ray photons per pixel. The number of photons per pixel that enter the detector 40 after attenuation by the object may be as small as one or two X ray photons per pixel, which the photomultipliers are sufficiently sensitive to detect.

As noted, the photomultiplier tubes 44 detect visible radiation that is instantaneously produced when the X ray pulses strike the scintillating screens 42 of the detector 40. In addition to these light photons, a plurality of delayed light photons are generated that subsist for a time comparable to the time required for a sweeping line of pencil-beams. This source of noise, called "afterglow", arises because of excitation of the photomultiplier tubes 44 (i.e., by the delayed light photons emitted by the scintillating screens) disposed at each level of the screens 42. Afterglow cannot be removed from conventional scintillating screens and is a limiting noise factor in pencil-beam detectors, or any detector using scintillating screens or scintillators with after-glow.

In accordance with the invention, the afterglow noise may be reduced by precisely controlling the sampling time of the photomultiplier tubes 44. As noted, the pulsed beams generated by the X-ray source 14 preferably have a duration of a few μsecs and are separated from adjacent pulses by longer than 0.1 msec. The sampling logic circuit 65 preferably comprises a string of delay elements that generate control signals that are synchronized to the pulse repetition rate of the source 14. When the X-ray pulses are intercepted by the detector 40, these control signals enable the outputs of the photomultiplier tubes, and other elements of the circuit 60, so that the outputs are sampled for only a few μsecs, which time period is equal to the duration of each X-ray pulse. This sampling period is immediately followed by a substantially longer quiescent period of time during which the photomultiplier tubes are not sampled, e.g., preferably at least 0.1 msec.

Figure 7A:
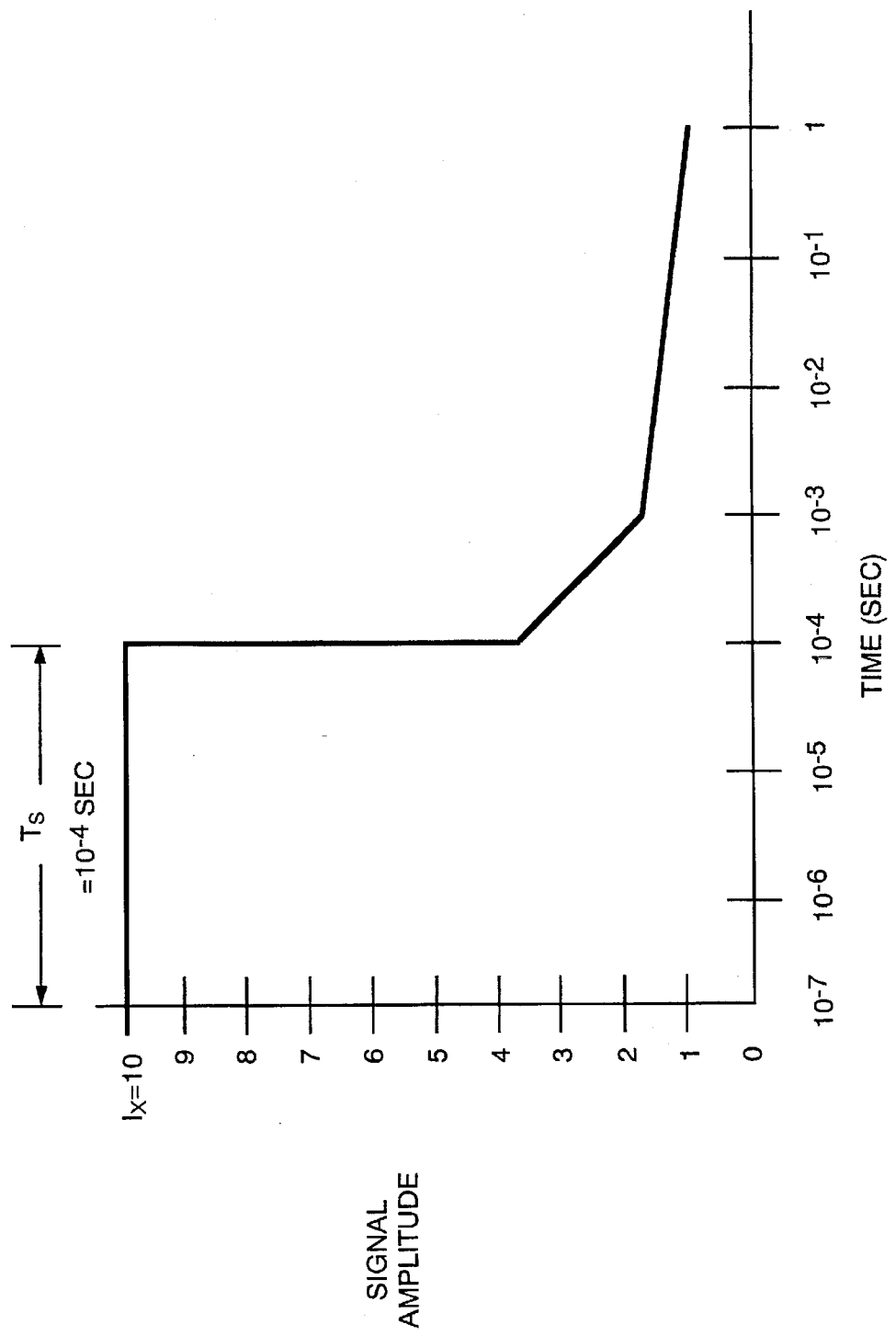
FIG. 7A is a graph depicting a prior art sampling technique.
Figure 7B:
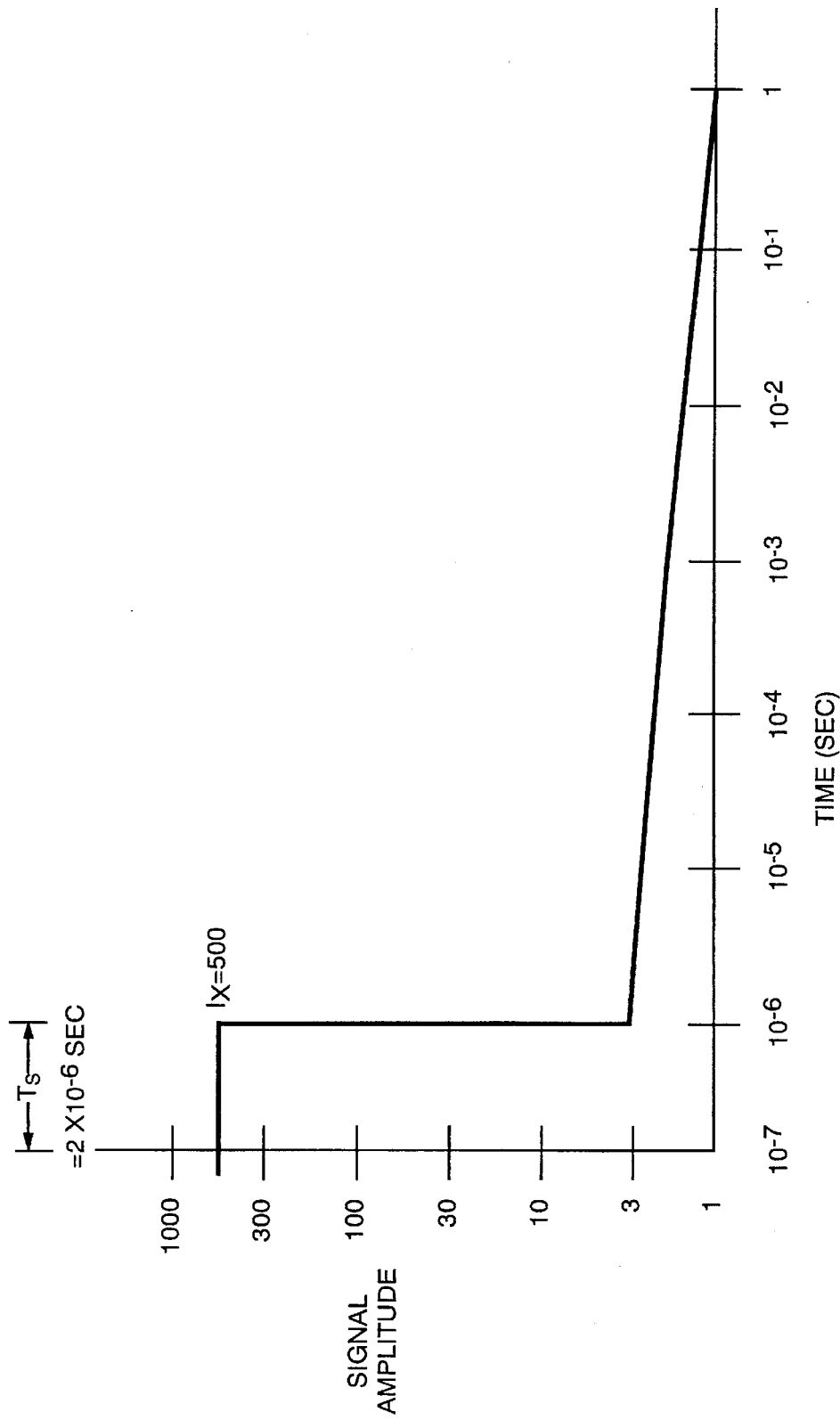
FIG. 7B is a graph depicting an improved sampling technique in accordance with the invention.

FIGS. 7A is a graph depicting a prior art sampling technique, while the graph of FIG. 7B depicts an improved sampling technique in accordance with the invention. In each of these cases, the total energy of the X-rays incident on the detector during the sampling time is the same. Thus, in FIG. 7A the intensity of the X-ray signal, $I_x$, times the sampling time, $T_S$ (i.e., $10 \times 10^{-4}$) equals $10^{-3}$. In FIG. 7B, $I_x$ times $T_S$ (i.e., $500 \times 2 \times 10^{-6}$) equals $10^{-3}$. In both cases the afterglow noise signals are the same, i.e., after $10^{-2}$ seconds, the amplitudes of the afterglow noise are two (2) arbitrary units.

Although the signal integrated over the pixel "dwell" time is identical in the two cases, the ratio of the signal to afterflow noise during the sampling time $T_S$ differs by a factor of 500/10=50. Thus, the signal to noise ratio is improved by a factor of the square root of 50, or approximately 7, if the sampling time of the detector is limited to the duration time of the X-ray signal as described herein.

In the illustrative embodiment, the ratio of sampling time to quiescent time is approximately 1:50, such that only 1/50th of the typical afterglow noise occurs during measurement of a useful X-ray signal.

In addition, the afterglow noise may be reduced by "turning-off" selected photomultiplier tubes. Referring again to FIGS. 4A and 6, as the X-ray pencil beam strikes the scintillating screens 42, those photomultipliers 44 that are not in the vicinity of the incident X rays are de-activated. De-activation of the tubes may be accomplished in connection with the electronic circuit 60 by disabling the outputs of the photomultiplier tubes since the location of the incident beam may be measured at the rotating cylindrical collimator 40. It should be noted that the magnitude of afterglow reduction is the ratio of functioning photomultiplier tubes to the total number of tubes.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. An improved X-ray inspection system for reducing afterglow noise during the inspection of an object, said improved system comprising:

a pulsed X-ray source for radiating a cone of X ray pulses that penetrate the object at a rate of at least about 2,000 pulses per second, said pulses being asserted for a duration period of time and adjacent of said pulses being separated by a separation period of time, said separation period being substantially longer than said duration period; and a detector for intercepting said X-ray pulses penetrating the object and for transforming said X-ray pulses into image data, said detector comprising at least one scintillating screen optically coupled to a plurality of photoemissive detecting elements such that when said X-ray pulses are intercepted by said detector, outputs of said photoemissive detecting elements are sampled for a sampling period of time immediately followed by a quiescent period of time during which said photoemissive detecting elements are not sampled, said quiescent period being substantially longer than said sampling period so as to significantly reduce afterglow noise during inspection of the object.

2. The improved X-ray inspection system of claim 1 wherein said separation period is approximately equal to said quiescent period and wherein said duration period is approximately equal to said sampling period.

3. The improved X-ray inspection system of claim 1 further comprising a rotating cylindrical collimator for converting said X-ray pulses into a pencil-beam of X-ray pulses.

4. The improved X-ray inspection system of claim 3 further comprising an enclosure for containing said source, said enclosure having an integrally-formed precollimator that limits said radiated cone to a fan-beam of X ray pulses.

5. The improved X-ray inspection system of claim 4 wherein said precollimator comprises a shield and a slit.

6. The improved X-ray inspection system of claim 5 further comprising a fixed-slit collimator arranged between said rotating cylindrical collimator and the object, said fixed-slit collimator further limiting said pencil-beam of X-ray pulses prior to penetrating the object.

7. The improved X-ray inspection system of claim 1 wherein said source is a high-energy pulsed linear accelerator having a repetition rate of about 2,000 to 10,000 pulses per second.

8. The improved X-ray inspection system of claim 1 wherein said source is a low-energy X-ray tube having a peak energy of 200 to 800 KeV.

9. The improved X-ray inspection system of claim 1 wherein said detector comprises a plurality of scintillating screens arranged in a back-to-back configuration to increase the efficiency of said detector.

10. The improved X-ray inspection system of claim 9 wherein said photoemissive detecting elements comprise photomultiplier tubes.

11. A method of reducing afterglow noise during inspection of an object by an X-ray inspection system, said method comprising the steps of:

generating X-ray pulses at a rate of least 2,000 pulses per second, wherein each of said pulses has a time duration that is substantially less than a separation of time between adjacent of said pulses;

intercepting said X-ray pulses using a scintillating screen optically coupled to a plurality of photoemissive detecting elements of a detector, each of said photoemissive detecting elements generating an electrical output signal in response to visible light produced by said scintillating screen; and sampling said outputs of said plurality of photoemissive detecting elements during said duration of time of said X-ray pulses to reduce the afterglow noise of said system.

12. Apparatus for reducing afterglow noise during inspection of an object by an X-ray inspection system, said apparatus comprising:

means for generating X-ray pulses at rate of at least about 2,000 pulses per second, wherein each of said pulses has a time duration that is substantially less than a separation of time between adjacent of said pulses;

means for intercepting said X-ray pulses using a scintillating screen optically coupled to a plurality of photoemissive detecting elements of a detector, said photoemissive detecting elements generating current at outputs thereof in response to visible light produced by said scintillating screen; and means for sampling said outputs of said plurality of photoemissive detecting elements during said duration of time of said X-ray pulses to thereby reduce the afterglow noise of said system.

* * * * *